United States Patent [19]

Jonsson

[11] Patent Number: 5,554,800
[45] Date of Patent: Sep. 10, 1996

[54] INSPECTION DEVICE FOR DETECTING SURFACE FAULTS, AND AN INSTRUMENT INCORPORATING SUCH A DEVICE

[75] Inventor: Ivar Jonsson, Onsala, Sweden

[73] Assignee: Vattenfall AB, Vallingby, Sweden

[21] Appl. No.: 211,616

[22] PCT Filed: Oct. 12, 1992

[86] PCT No.: PCT/SE92/00716

§ 371 Date: Jul. 27, 1994

§ 102(e) Date: Jul. 27, 1994

[87] PCT Pub. No.: WO93/07475

PCT Pub. Date: Apr. 15, 1993

[30] Foreign Application Priority Data

Oct. 10, 1991 [SE] Sweden .................................. 9102939

[51] Int. Cl.$^6$ .......................... G01N 21/91; G01N 21/90
[52] U.S. Cl. ........................ 73/104; 73/865.8; 73/866.5
[58] Field of Search ........................ 73/104, 40.7, 866.5, 73/865.8, 40.5 R; 250/302; 376/249, 250, 251

[56] References Cited

U.S. PATENT DOCUMENTS

| | | | |
|---|---|---|---|
| 2,667,070 | 1/1954 | Sockman et al. | 73/104 |
| 3,049,752 | 8/1962 | Jorda et al. | 73/104 |
| 3,830,094 | 8/1974 | Leger | 73/104 |

FOREIGN PATENT DOCUMENTS

| | | | |
|---|---|---|---|
| 0337700 | 10/1989 | European Pat. Off. | |
| 2358802 | 5/1975 | Germany | 73/104 |
| 119035 | 9/1980 | Japan | 73/40.5 R |
| 196129 | 12/1982 | Japan | 73/40.7 |
| 246647 | 11/1986 | Japan | 73/49.1 |
| 123127 | 5/1989 | Japan | 73/104 |
| 938046 | 6/1982 | U.S.S.R. | 73/40.5 R |
| 977502 | 12/1964 | United Kingdom | 73/104 |
| 1207090 | 7/1970 | United Kingdom | 73/49.1 |

*Primary Examiner*—Hezron E. Williams
*Assistant Examiner*—Daniel S. Larkin
*Attorney, Agent, or Firm*—Jacobson, Price, Holman & Stern, PLLC

[57] ABSTRACT

For the purpose of detecting the presence of surface flaws in tubular members, the surface to be inspected is first coated with penetrant and any excessive penetrant then removed. A device is then moved along the tubular member until that part of the surface to be inspected is reached, whereafter the device is expanded into abutment with this tubular surface. Penetrant that has entered a surface flaw is transferred to the surface of the device, where it can be made visible and studied, subsequent to having constricted the device and removed it from the tubular member. An instrument is provided which includes the device so as to enable a tubular member to be pre-treated with penetrant and penetrant transferred to the surface of the device.

20 Claims, 2 Drawing Sheets

INSPECTION DEVICE FOR DETECTING SURFACE FAULTS, AND AN INSTRUMENT INCORPORATING SUCH A DEVICE

TECHNICAL FIELD

The invention relates to a device and to an instrument for the non-destructive testing of tubular members, by discovering, localizing and reproducing surface flaws and faults such as cracks that may be present in the inner surfaces of the tubular members. The invention finds particular application in the inspection of tubular members of small inner diameters.

TECHNICAL STANDPOINT

Heat exchangers such as steam generators in nuclear power stations are equipped with high-load heat exchanger tubes having an internal diameter of 15–20 mm. The tubes are secured by rolling the tubes in end walls which form tube attachments and partition walls that mutually separate the heat-carrying media passing through the heat exchangers. The vulnerability of the tubes to load caused by pressure and heat and by changes in these factors, vibrations, corrosion, etc., can result in flaws and faults, such as the formation of cracks in the tube walls. If these flaws are not rectified in time, the flaws may become so serious as to cause the tubes to rupture, resulting in serious consequences. It is therefore important to constantly monitor the tubes, so that necessary measures can be taken in time. In the case of steam generators, damaged tubes can be plugged at the time of making an annual inspection.

Different non-destructive testing techniques are used to detect surface flaws, of which techniques inductive testing has been one of the few techniques applied for testing deep into small bore pipes and tubes. In this technique, there is inserted into the tubular member to be tested a probe which is equipped with a coil to which alternating current is supplied and which functions to induce eddy currents in the wall of the tubular member which retroact on the coil. Because the eddy currents are influenced by flaws in the tubular member, some information can be obtained as to whether or not a flaw exists and, if so, the size of the flaw, by measuring the retroactive effect of the eddy currents on the coil. One pronounced drawback with this known method of inspection, however, resides in the difficulty experienced in determining the nature of the flaw, and in that the signal interference ratio is small. Not only small flaws are hidden by interference noise. For instance, if the probe is constructed to produce good indications of the presence of longitudinally extending cracks, which are the most common, equally as large transversely extending cracks will only result in small readings (output signals) which are difficult to distinguish in the interference noise.

DISCLOSURE OF THE INVENTION

Technical Problem

The object of the present invention is to provide a device and an instrument for detecting internal surface flaws in tubular members. The device is intended to provide a more accurate understanding of the flaws than has hitherto been possible with known methods.

Solution

This object is achieved with an inventive device and an inventive instrument.

In the case of one known method for the non-destructive testing of surfaces, flaws which are otherwise invisible are treated so that they can be seen with the naked eye. A so-called penetrant, i.e. a liquid which is able to penetrate into very fine cracks, is applied to the test surface with the aid of a brush for instance. The penetrant also has the ability to remain in the surface fault when the test surface is subsequently washed to remove excessive penetrant that has not penetrated into the surface faults. When a coloured penetrant is used, the test surface is sprayed with a so-called developer which contains a fine-grain white powder. The penetrant is drawn out of the cracks by the powder layer and disperses in the layer so as to form contrasting indications on cracks having a width down to 0.001 mm. On the other hand, when a fluorescent penetrant is used, it is possible to observe indications directly with the aid of ultraviolet light. This method, however, presumes that the test surface can be easily reached. Consequently, it has not been possible to apply this method on the internal surfaces of long, narrow tubular members.

The present invention also includes the treatment of a test surface with a penetrant and the removal of excessive liquid. However, instead of viewing the indications directly on the test surface, the penetrant taken-up by the fault or flaw is transferred to the surface of a device such as to leave an imprint of the indication and the device is then removed from the inaccessible site of the flaw. This imprint can then be studied in some appropriate manner. In order to obtain an effective image transfer and to prevent the transferred indications from being impaired as the device is removed from the tubular member, it is proposed that the inspection device is expandable. Thus, the device is inserted into the tubular member and brought to the inspection site while reduced in diameter to a size which will permit the device to move through the tubular member in a generally frictionless fashion, whereafter the device is expanded so as to bring the outer surfaces of the device into effective contact with the test surface. When penetrant has been transferred, the device is then constricted to an extent which will enable it to be moved in the tubular member essentially in a frictionless fashion and without risk of the indications being scraped from the surfaces of the device as it is moved out of the tubular member.

The inspection device shall thus have two functions. Firstly, the device shall include a body which can increase in thickness so as to conform to the interior shape of the tubular member and also to decrease in thickness, and, secondly, the device shall include surfaces which can be brought into contact with the inner surfaces of the tubular member and absorb penetrant, and possibly also disperse said penetrant so as to provide readily observed indications, and to retain these indications for the length of time required to carry out said observations. These two operational modes can be achieved with one and the same element, or alternatively the device may, for instance, be comprised of an expandable body and stretchable sheeting which surrounds said body and onto which penetrant can be transferred.

The body can be made expandable in several different ways. For instance, the body may have an elastic construction and include a cavity or hollow into which pressure medium is introduced, or the end walls of a normally cylindrical body may be pressed towards one another. A suitable surface is obtained when the body or the surrounding sheeting is made of a polymeric material, such as polyurethane. An outer surface which possesses the aforesaid desired properties can be obtained when the contact surface of the body or the penetrant absorbing sheeting has a structure which exhibits a large number of shallow pits, such as the surface structure obtained by fine-grinding processes.

In order to enable the invention to be applied industrially, there is proposed an instrument which, in addition to the inspection device, includes a device for applying penetrant to and removing excessive penetrant from an internal tubular surface, and a device for handling the inspection device and the penetrant applying device and for introducing said devices into the tubular member and removing the same therefrom. The instrument may also include a member which functions to dry-up any rinsing liquid that remains in the tubular member. The inspection device and the penetrant applying and rinsing device are mounted in line with one another with the surface drying member located therebetween, so as to form a unit whose one end is attached to one end of the handling device.

The penetrant applying and rinsing device includes two mutually spaced, closed walls whose peripheral surfaces are intended to seal against a surrounding tubular surface. These walls thus delimit a space in the interior of the tubular member, the wall surface located between the seals being the subject of a penetrant application and rinsing operation. The space is first filled completely with penetrant through one of the media conveying lines connected to the handling device. The liquid penetrant is then allowed to act over a period of time, whereafter the space is emptied and the space then flushed with clean water so as to rinse the wall surfaces clean.

The space is then emptied of rinsing water and the unit as a whole is then displaced with the aid of the handling device to a position in which the drying member is located within the region of the tubular surface to which penetrant has been applied and which has been subsequently rinsed. The drying member includes a part which, similar to the expandable inspection device, can be caused to expand or swell and made to conform to the shape of the tubular inner surface and pressed thereagainst. Since that part of said component which is pressed against the tubular surface is comprised of a liquid-absorbent material, the component will remove any residual droplets of surface rinsing water.

The drying member is then constricted to a smaller diameter and the whole of the unit is moved further along the tubular member to a position in which the inventive inspection device is located within the penetrated, rinsed and dried region of the tubular wall. Any penetrant that has penetrated a flaw, e.g. crack, is then transferred to the surface of the inspection device in the aforedescribed manner. The unit is then withdrawn from the tubular member, with the aid of the handling device, for study of those indications that may be imprinted on the surface of said device.

The handling device may, for instance, have the form of a tube or, when testing curved tubular members, may have the form of a flexible but rotationally rigid hose through which the conductors required to operate the unit are drawn. Because movement of the unit in the tubular member is solely translatory, an indication of the location of an indicated surface flaw or fault in the tubular member can be obtained by recording the distance through which the unit is inserted. These imprints can be recorded with the aid of known optical techniques and documented as a stage in routine safety checks.

The invention can be used in tubular members of different sizes and intended for different purposes, for instance in the tubes of steam boilers and different process equipment. The invention is not limited to the non-destructive testing of standard tubular members. It can also be used effectively for inspecting, for instance, square tubular members of non-uniform crossdimensions. Neither is the invention restricted to the use of optically readable indications. For instance, the penetrant may contain a radioactive substance and therewith enable other reading methods to be applied.

Advantages

Application of the invention provides an effective supplement to other inspection methods, so as to enable a more universal inspection to be carried out. The same feed mechanism that is used to insert other instruments into the tubes of steam generators can also be used to feed the inventive unit into and out of a tubular member. The ability to operate at distances through lines enables different operating means, such as pumps, etc., to be located at the most suitable places.

BRIEF DESCRIPTION OF THE DRAWINGS

The present invention will now be described in more detail with reference to a preferred exemplifying embodiment thereof and also with reference to the accompanying drawings, in which like parts have been identified like reference numerals.

For the sake of illustration, the instrument is shown compressed longitudinally and some of the elements have been overdimensioned.

DESCRIPTION OF A PREFERRED EMBODIMENT

Figure 1:
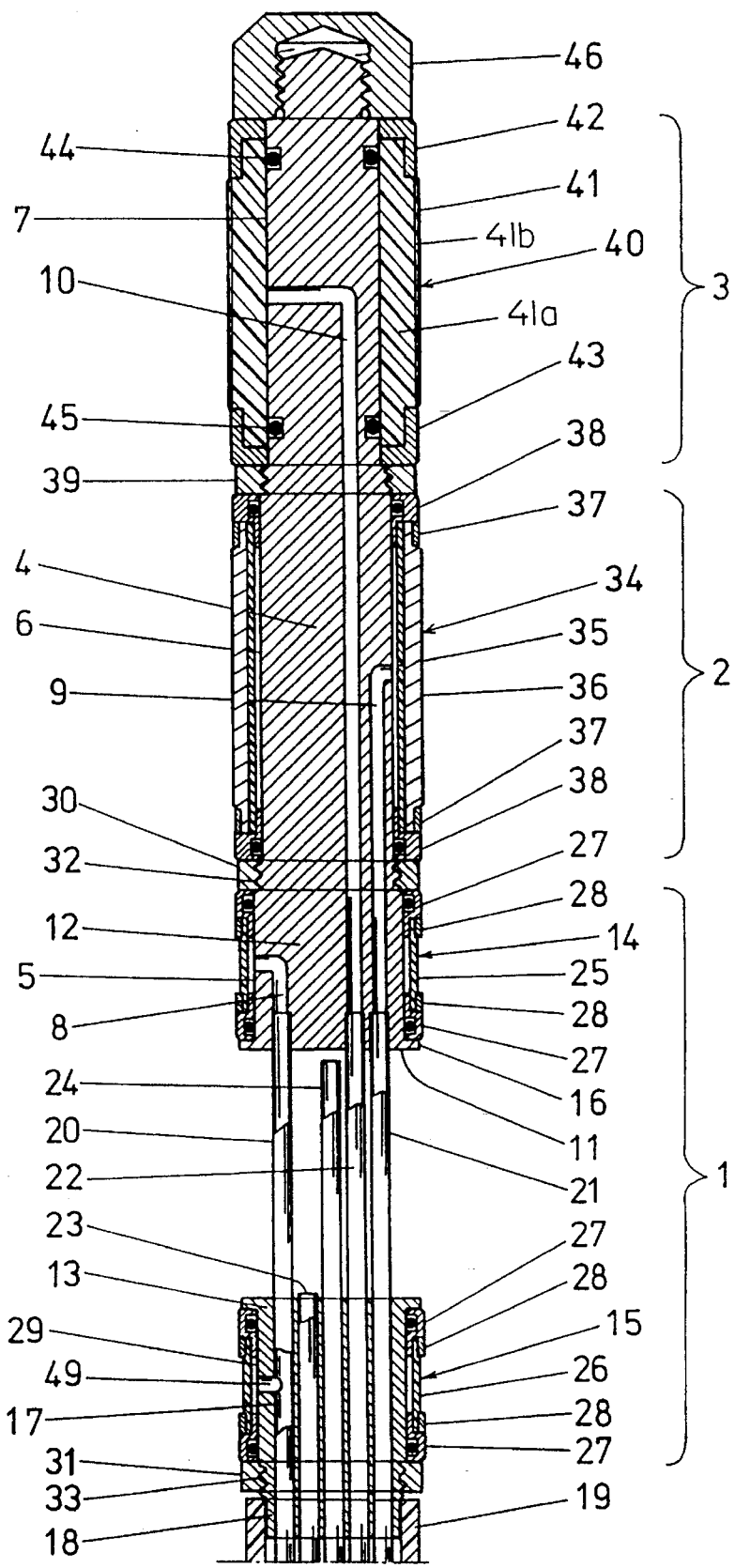
FIG. 1 is a longitudinal section view illustrating the preferred embodiment of the instrument and the inspection device.

A preferred embodiment of an inventive instrument includes a probe which is normally used in an upstanding position, and a handling device which is used to manoeuver the probe and which in the illustrated embodiment comprises a number of hoses housed in a flexible tubular casing attached to the probe. The hoses function to conduct various media and are connected at one end to pipes provided in the probe, as described below, while the other ends of respective hoses are connected to a service unit which includes pumps, control equipment, etc. As will be seen in FIG. 1, the probe comprises three main parts. A first main part 1 is intended for applying penetrant to a test surface and for rinsing away excessive penetrant. A second main part 2 is intended for drying the test surface, while the third main part 3 is intended to image possible surface flaws in the test surface. All of the main probe parts include expandable functional elements. These elements may be of the kind which can be expanded by exerting pressure from the sides thereof. In the case of the illustrated embodiment, however, the expandable elements include cavities or hollows and are expanded by placing the cavities under pressure with the aid of a medium introduced through the aforesaid hoses.

The probe body has in the form of a tool-machined shaft 4 whose cylindrical outer surface includes three in-line cylindrical surfaces 5, 6 and 7. As will be seen from FIG. 1, the diameters of the cylindrical surfaces decrease in an upward direction and each of said surfaces provides a position for the respective functional elements of the three main parts of the probe. Three pressure-media conducting channels 8, 9 and 10 are drilled in the shaft 4. The first channel openings are located in the lower end-surface 11 of the shaft, while each of the second channel openings are located in a respective cylindrical surface 5, 6 and 7.

The main probe part 1 intended for applying penetrant and rinsing away excessive penetrant includes two coaxial and mutually spaced plungers 12, 13, each of which is provided with respective functional elements 14, 15 which serve as gas,tight seals in delimiting a space in which the tubular member shall be inspected or tested. The first plunger 12 is formed by the lower part of the shaft 4 and includes the cylindrical surface 5, which is the surface that has the largest diameter. This cylinder surface forms a position for solely one of the two sealing units of said main probe part and is much shorter than the other two cylinder surfaces 6, 7 on the shaft. The bottom of the plunger 12 is terminated with a flange or lip 16 whose outer diameter is slightly smaller than the inner diameter of the tubular member to be inspected.

The second plunger 13 located below the first mentioned plunger 12 is comprised of the upper end of a further element, called structural element 17, whose upper part has a configuration identical to the configuration of the first plunger 12 but in mirror image. The lower end 18 of the structural element 17 is cylindrical and has a diameter which is adapted to form an attachment for the earlier mentioned flexible tubular casing of the flexible handling device 19 by means of which the probe is manoeuvred in the tubular member. The structural element 17 is provided with five penetrating throughlets which sealingly accommodate five pipes, of which three, 20, 21 and 22, extend up past the interspace between the structural element 17 and the end surface 11 of the shaft 4 and are sealingly connected at this end surface to the aforesaid channels 8, 9 and 10. As before mentioned, these pipes are connected to the hoses in the casing 19 and also form a bridge by means of which the plungers are connected to one another. Of the two remaining pipes, one pipe functions as an inlet and outlet pipe 23 and is open at the upper end surface of the structural element 17, whereas the other pipe functions as an overflow 24 and extends through practically the entire interspace and is terminated immediately beneath the end surface 11 of the shaft 4.

Each of the mutually identical sealing units 14, 15 includes a hose piece 25, 26 made of a flexible material, such as a silicone polymer, having straight cut ends, a pair of terminal rings 27 which are reduced in diameter to form collars on which the ends of the hose pieces are fitted, and a pair of clamping rings 28 for securing the hose ends on the collars of the terminal rings. The terminal rings have cylindrical inner surfaces whose diameters slightly exceed the diameter of the lowermost cylinder surface 5 on the shaft 4 and which are fitted with internal O-ring grooves and corresponding O-rings. The sealing units 14, 15 have the same length as the aforesaid cylinder surface 5 and thus also a corresponding surface 29 on the structural element 17 and are mounted on said surfaces and locked by first lock nuts 30, 31 through the agency of screw threads 32, 33 provided externally of respective cylinder surfaces on the shaft and the structural element.

The second main probe part 2 intended for drying the rinsed surfaces of the tubular member comprises a functional element in the form of a drying unit 34 which is mounted on the intermediate cylinder surface 6 of the shaft 4 and the length of which corresponds to the length of said intermediate cylinder surface 6 and slightly exceeds the distance between the structural element 17 and the shaft 4. The drying unit 34, is constructed in a manner similar to the aforedescribed sealing units, but with the exception that it is much longer than said units. The drying unit also includes an elastic hose 35, made of a silicone polymer for instance, on the outside of which there is fitted a sleeve 36. The sleeve 36 consists of a water-absorbent sheeting, for instance a porous nonwoven cloth, whose length is equal to the length of the hose 35 and the ends of which sheeting and hose are clamped between a pair of clamping rings 37 and terminal rings 38 of the same kind used with the sealing units. The inner diameter of the terminal rings is slightly larger than the diameter of the intermediate cylinder surface and the rings are provided with 0-rings which seal against said cylinder surface. The whole of the drying unit is mounted on the cylinder surface in abutment with the first lock nut 30 which secures the sealing unit 14 on the shaft 4. The drying unit is locked against axial movement on the shaft 4 by the second lock nut 39 screwed on said shaft.

The third main probe part 3 that functions as an expandable body for imaging surface flaws has a functional element in the form of a inspection unit 40 mounted on the uppermost cylinder surface 7 of the shaft. As will be seen from FIG. 1, the unit 40 has the same length as the cylinder surface 7. The inspection unit comprises an inspection tube 41 which is stepped down at respective ends thereof so as to receive two end sleeves 42, 43. The inspection tube is made of an elastic material 41a, such as polyurethane having a finely ground outer cylindrical surface, having an absorbent surface 41b provided thereon in the form of a casing. The distance between the two stepped ends of the tube 41 is somewhat shorter than the distance between the plungers 12, 13 and the outer diameter of said tube is adapted to the diameter of the tubular member to be inspected. Similar to the end sleeves 42, 43, the tube 40 has an inner diameter which corresponds to the diameter of the cylinder surface 7. Two O-rings 44, 45 are mounted in the outer surface of the shaft 4 and function to seal against the tube 41 inwardly of the end sleeves. The inspection unit 40 is locked against axial movement on the shaft 4 in abutment with the second lock nut 39 by an end nut 46 which is screwed on a corresponding screw thread at the top of the shaft.

Method of Operation

A robot positions a feed mechanism (not shown) in the lower part of a steam generator, beneath the tubular member 47 chosen for examination. The feed mechanism then pushes the instrument probe up into the tube, with the aid of the probe handling device 19, until the two plungers 12, 13 of the penetrant applying and penetrant rinsing main probe part 1 lie above and beneath a desired inspection area 48, of the tubular member (see FIG. 2a). Air pressurized to about 2 bars is injected from the service unit into the spaces located inside of the hose pieces 25, 26 of the sealing units, via the pipe 20, a radial hole 49 in the plunger 13 to the pipe 20, and the passage 8, so as to press the sealing units 14, 15 outwardly and therewith provide a seal between the plungers 12, 13 and the surrounding tubular member. Subsequent to having delimited an inspection space 50 in the tubular member, including the inspection area 48, the space is filled with a penetrant which is pumped from the service unit through the inlet and outlet pipe 23, until penetrant passing through the overflow pipe 24 and associated hose in said casing runs out through the hose outlet in the service unit, whereupon the supply of penetrant is discontinued. The inspection space 50 has then been filled essentially completely, due to the flow resistance in the overflow pipe and associated hose. The penetrant is then allowed to act for a given period of time, whereafter the space is emptied through the inlet and outlet pipe 23 with the aid of said pump, with a reversed pumping action.

Cleaning water is then delivered to the inspection space 50 in the same manner as the penetrant. This water flows through the space to the overflow pipe 24 and rinses the inspected surface over a period of time, whereafter the space is emptied by reversing the pump.

Figures 2A, 2B, 2C:
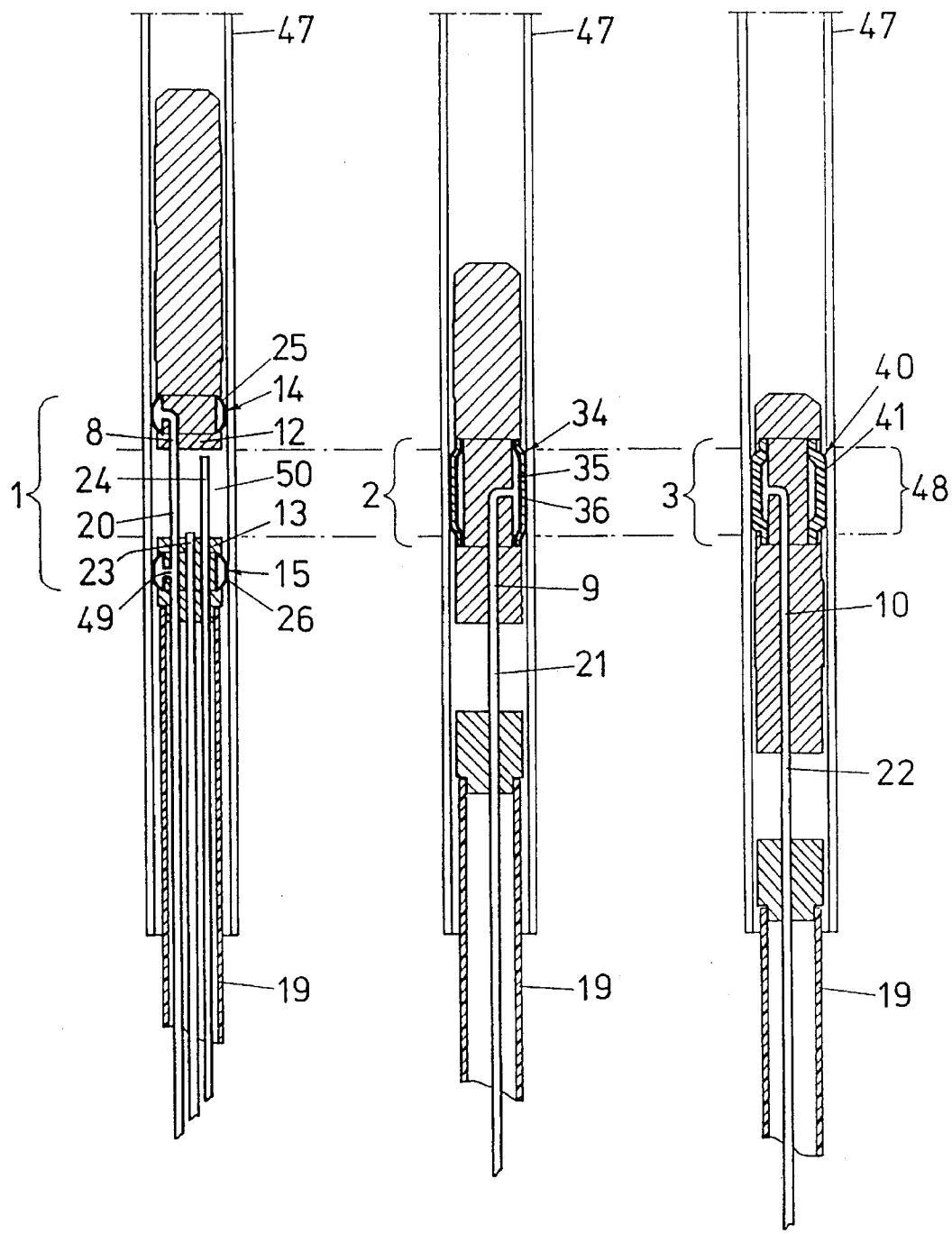
FIGS. 2a, 2b and 2c illustrate the modus operandi of the instrument in three stages, with the active components being shown in each step.

Pressure on the sealing units 14, 15 is then relieved so that the sealing units will return to their original state, whereafter the entire probe is moved down in the tubular member 47 with the aid of the probe handling device 19 and the feed mechanism, until the main probe part 2 intended for drying the inspected area is located within the inspection area 48 (FIG. 2b). Air under a pressure of about 2 bars is then introduced from the service unit, through the pipe 21 and the passage 9, so as to press the elastic hose 35 of the drying unit 34 uniformly against the tubular member 47, with the water absorbent sleeve 36 between the hose and said tubular member. The sleeve will therewith soak up any water droplets that remain. Subsequent to interrupting pressurization of the elastic hose 35 and after the elastic hose has returned to its original state, the sleeve 36 is permitted to expand so as to further increase its absorbency. The rinsed surface can be dried in several stages, by withdrawing the probe in small consecutive steps.

When penetrant has been delivered to the inspection area of the tubular member and excessive penetrant has been removed, the probe is then drawn down through a distance which will bring the imaging main part of the probe within this treated area (see FIG. 2c). Pressurized hydraulic fluid is then delivered from the service unit through the pipe 22 and the passage 10 to the interior of the tube 41 so as to expand the tube and press it against the inner wall of the tubular member, so as to transfer any penetrant that has penetrated a flaw to the surface of the inspection tube. The hydraulic fluid is delivered at a pressure of about 70 bars, which corresponds to the differential pressure to which the steam generator tubes are subjected in operation. The hydraulic fluid is then evacuated from the inspection tube, so that the tube will return to its original state and the probe can be withdrawn from the tubular member 47. The whole of the process described, including robotics guiding of the instrument, the operation of the instrument feeding mechanism, the operation of the service unit, etc., can be controlled by a computer. Subsequent to having removed the probe from the tubular member, the drying member 34 and the inspection unit 40 can be removed from the shaft, by removing the two uppermost nuts 39, 46, therewith enabling two fresh units to be mounted on the shaft in preparation for another inspection.

I claim:

1. A device for use in detecting surface penetrant containing faults or flaws in the inner surface of a tubular member, the device comprising:

a handling device and a tubular shaped body of an elastic material having penetrant absorbent surfaces;

said tubular shaped body being movable by said handling device to an area of the inner surface of said tubular member chosen for inspection, expanded to a state in which the penetrant absorbent surfaces abut the entire inner surface of said tubular member surrounding said penetrant absorbent surfaces, and contracted so as to distance the penetrant absorbent surfaces from the inner surface of said tubular member and removal of said tubular shaped body by said handling device.

2. A device according to claim 1, wherein the absorbent surfaces have a structure which exhibits a large number of minute pits, similar to the configuration of a surface that has been finely ground.

3. A device according to claim 1, wherein the absorbent surfaces are provided on an elastic covering in the form of a casing which is comprised by said body.

4. An instrument for use when detecting surface faults or flaws in tubular members, including the device according to claim 1, wherein the instrument also includes means for delivering penetrant to said area of the inner surface of the tubular member chosen for inspection; and said means is combined with the device to form an inspection probe; said means includes two units which are mutually spaced in the longitudinal direction of the tubular member and which seal the surrounding tubular member such as to form in said tubular member a substantially closed, limited space which can be filled with penetrant; and the inspection probe is movable in the tubular member between a first position in which said area of the inner surface of said tubular member selected for inspection is included between the sealing units, and a second position in which the device is surrounded by said area of the inner surface selected for inspection.

5. An instrument according to claim 4, wherein the inspection probe occupies said first position when a liquid delivery and removal line is connected to the bottom part of the space and an overflow line is connected to the upper part of said space.

6. An instrument according to claim 4, wherein the inspection probe also includes an expandable member with a cover of a liquid-absorbent material; and the inspection probe can be displaced in the tubular member at least to a third position in which said expandable member is surrounded by said area of the inner surface chosen for inspection.

7. An instrument according to claim 6, wherein the expandable member is located between said device and said penetrant delivering means.

8. An instrument according to claim 4, wherein the handling device has the form of a tube or a flexible but rotationally rigid hose and is connected at one end thereof to the inspection probe.

9. A device for use in detecting surface faults or flaws in the inner surface of a tubular member, the device comprising:

an elastic body having penetrant absorbent surfaces; said elastic body being movable to an area of the inner surface of said tubular member chosen for inspection, expanded to a state in which the absorbent surfaces abut the inner surface of said tubular member, and contracted so as to distance the absorbent surfaces from the inner surface of said tubular member, said absorbent surfaces being provided on an elastic covering in the form of a casing which is comprised by said body.

10. An instrument for use in detecting surface faults or flaws in the inner surface of a tubular member, the device comprising:

an elastic body having penetrant absorbent surfaces; said elastic body being movable to an area of the inner surface of said tubular member chosen for inspection, expanded to a state in which the absorbent surfaces abut the inner surface of said tubular member, and contracted so as to distance the absorbent surfaces from the inner surface of said tubular member, means for delivering penetrant to said area of the inner surface of the tubular member chosen for inspection and said means being combined with said elastic body to form an inspection probe;

said means including two units which are mutually spaced in the longitudinal direction of the tubular member and which seal the surrounding tubular member such as to form in said tubular member a substantially closed, limited space which can be filled with penetrant; and the inspection probe being movable in the tubular member between a first position in which said area of the inner surface of said tubular member selected for inspection is included between the sealing units and a second position in which the device is surrounded by said area of the inner surface selected for inspection.

11. An instrument according to claim 10, wherein the inspection probe occupies said first position when a liquid delivery and removal line is connected to the bottom part of the space and an overflow line is connected to the upper part of said space.

12. An instrument according to claim 10, wherein the inspection probe also includes an expandable member with a cover of a liquid-absorbent material; and the inspection probe can be displaced in the tubular member at least to a third position in which said expandable member is surrounded by said area of the inner surface chosen for inspection.

13. An instrument according to claim 12, wherein the expandable member is located between said device and said penetrant delivering means.

14. An instrument according to claim 10, wherein the inspection probe includes a probe handling device for manoeuvering the inspection probe and the handling device has the form of a tube or a flexible but rotationally rigid hose and is connected at one end thereof to the inspection probe.

15. A device for use in detecting surface penetrant containing faults or flaws in the inner surface of a tubular member, the device comprising:

a handling device and an elastic body having penetrant absorbent surfaces;

said elastic body being movable by said handling device to an area of the inner surface of said tubular member chosen for inspection, expanded to a state in which the absorbent surfaces abut the inner surface of said tubular member, and contracted so as to distance the absorbent surfaces from the inner surface of said tubular member and removal of said elastic body by said handling device, said absorbent surfaces being provided on an elastic covering in the form of a casing which is comprised by said body.

16. An instrument for use in detecting surface penetrant containing faults or flaws in the inner surface of a tubular member, the device comprising:

a handling device and an elastic body having penetrant absorbent surfaces;

said elastic body being movable by said handling device to an area of the inner surface of said tubular member chosen for inspection, expanded to a state in which the absorbent surfaces abut the inner surface of said tubular member, and contracted so as to distance the absorbent surfaces from the inner surface of said tubular member and removal of said elastic body by said handling device, means for delivering penetrant to said area of the inner surface of the tubular member chosen for inspection;

said means being combined with the device to form an inspection probe;

said means including two units which are mutually spaced in the longitudinal direction of the tubular member and which seal the surrounding tubular member such as to form in said tubular member a substantially closed, limited space which can be filled with penetrant; and the inspection probe being movable in the tubular member between a first position in which said area of the inner surface of said tubular member selected for inspection is included between the sealing units, and a second position in which the device is surrounded by said area of the inner surface selected for inspection.

17. An instrument according to claim 16, wherein the inspection probe occupies said first position when a liquid delivery and removal line is connected to the bottom part of the space and an overflow line is connected to the upper part of said space.

18. An instrument according to claim 16, wherein the inspection probe also includes an expandable member with a cover of a liquid-absorbent material; and the inspection probe can be displaced in the tubular member at least to a third position in which said expandable member is surrounded by said area of the inner surface chosen for inspection.

19. An instrument according to claim 18, wherein the expandable member is located between said device and said penetrant delivering means.

20. An instrument according to claim 16, wherein the handling device has the form of a tube or a flexible but rotationally rigid hose and is connected at one end thereof to the inspection probe.

* * * * *